United States Patent [19]

Fischel

[11] 4,366,051

[45] Dec. 28, 1982

[54] HEMODIALYSIS SYSTEM

[76] Inventor: Halbert Fischel, 14802 Newport Ave., Apt. 2D, Tustin, Calif. 92680

[21] Appl. No.: 743,222

[22] Filed: Nov. 19, 1976

[51] Int. Cl.$^3$ ............................................. B01D 31/00
[52] U.S. Cl. .................................. 210/96.2; 210/134; 210/180; 210/181; 210/188; 210/195.2; 210/321.3; 422/26
[58] Field of Search ..................... 210/321 B, 180, 186, 210/134, 137, 188, 494 M, 22, 436, 321.1–321.5, 96.2, 181, 195.2; 55/184, 200, 204, 158, 189; 21/94, 97, 56; 137/504; 422/14, 26, 38

[56] References Cited

U.S. PATENT DOCUMENTS

| | | | |
|---|---|---|---|
| 1,449,406 | 3/1923 | Householder | 219/306 |
| 1,468,434 | 9/1923 | Zander | 137/504 |
| 1,756,008 | 4/1930 | Soprani | 219/306 |
| 2,617,765 | 11/1952 | Swarr | 210/134 |
| 3,064,649 | 11/1962 | Fuson | 55/200 |
| 3,352,779 | 11/1967 | Austin et al. | 210/321 B |
| 3,441,136 | 4/1969 | Serfass et al. | 210/321 B |
| 3,515,275 | 6/1970 | Bowman | 210/22 |
| 3,527,700 | 9/1970 | Goldhaber | 210/22 |
| 3,626,670 | 12/1971 | Pecker | 210/321 B |
| 3,669,880 | 6/1972 | Marantz et al. | 210/22 |
| 3,715,863 | 2/1973 | Zanoni | 55/204 |
| 3,809,241 | 5/1974 | Alvine | 210/321 B |
| 3,878,095 | 4/1975 | Frasier et al. | 210/321 B |
| 4,018,684 | 4/1977 | Uffer | 210/321 B |
| 4,026,800 | 5/1977 | Friedrich et al. | 210/321 B |
| 4,055,496 | 10/1977 | Friedrich et al. | 210/321 B |
| 4,060,485 | 11/1977 | Eaton | 210/321 B |
| 4,069,155 | 1/1978 | Tsujimoto et al. | 210/195 R |
| 4,137,160 | 1/1979 | Ebling et al. | 210/22 A |

FOREIGN PATENT DOCUMENTS 518924  11/1955  Canada ................................ 137/504

OTHER PUBLICATIONS

The American Heritage Dictionary of the English Language William Morris, Editor; Houghton Mifflin Company, Boston; 1976, p. 89.

*Primary Examiner*—David R. Sadowski
*Attorney, Agent, or Firm*—Fraser and Bogucki

[57] ABSTRACT

A compact self-sterilizable proportioning hemodialysis system alternatively usable with either a coil type or parallel flow artificial dialyzer without material alteration comprises a hydraulic driven dialysate proportioning pump in a positive pressure flow path to provide dialysate in a controlled concentration to a dialysate receiving canister. A coil-type dialyzer within the canister receives dialysate in a recirculating flow from a circulation pump. A venturi in the recirculating flow path provides a negative pressure to pull dialysate through a suction loop, which may alternatively include a parallel flow dialyzer. A conductivity cell, temperature monitor and blood leak detector sample and monitor dialysate from the canister, and to control the dialysate and indicate fault conditions. The system may alternatively function as a recirculating plate-type dialyzer having high dialysis efficiency. In this mode a vortex degasifier recirculating loop and an air separator in the suction loop eliminate entrained gases. Parts of the system may be sterilized by internal means, because the system defines a closed path when certain connections are made. An upright resistive heating steam generator delivers sterilizing steam throughout the liquid flow path which terminates in a pressure relief valve. This increases the steam temperature above the atmospheric water vaporization temperature and maintains the steam at a uniform temperature-pressure equilibrium throughout the flow path. The system requires no central dialysate mixing, yet closely controls the concentration of dialysate utilized.

11 Claims, 3 Drawing Figures

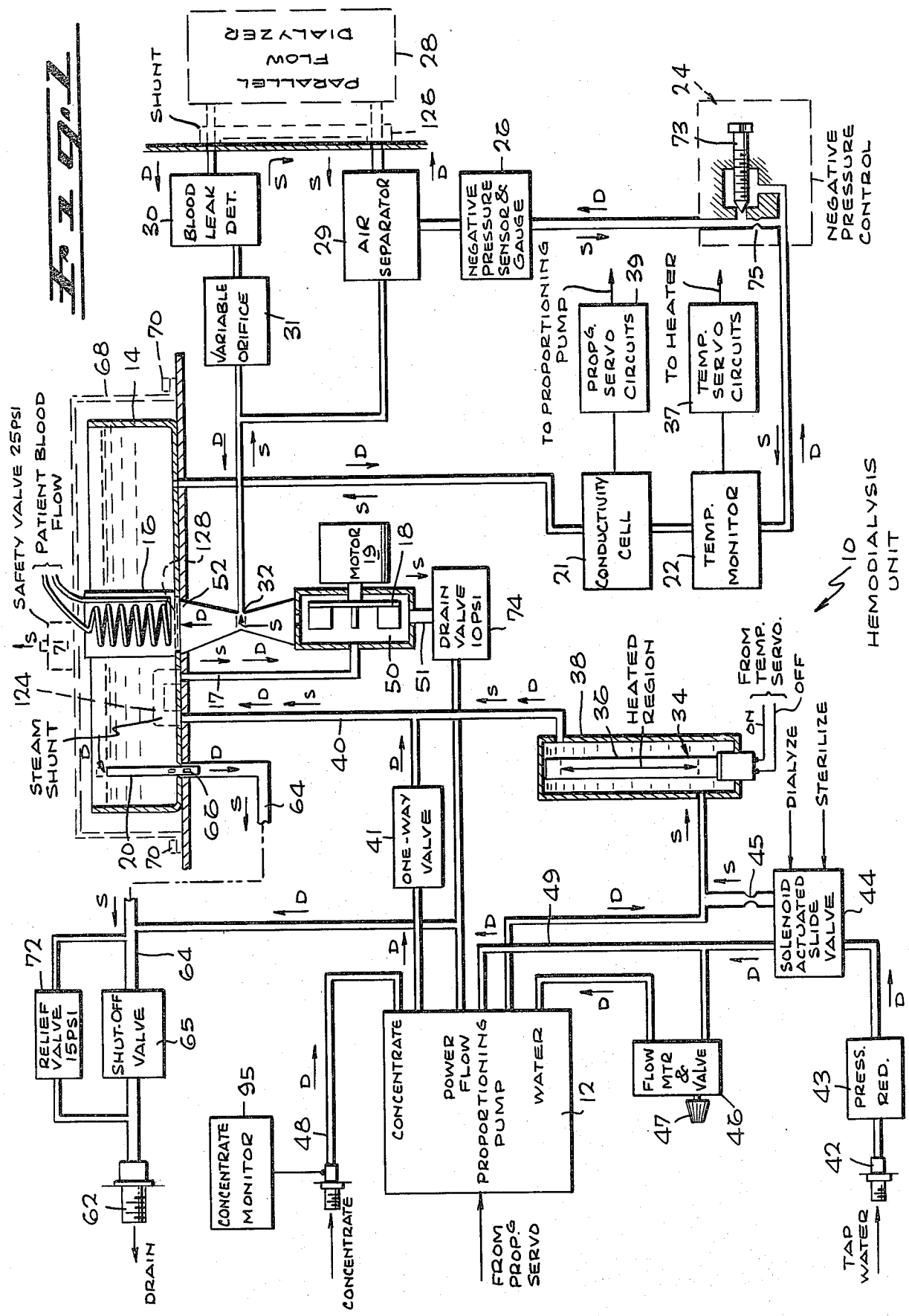

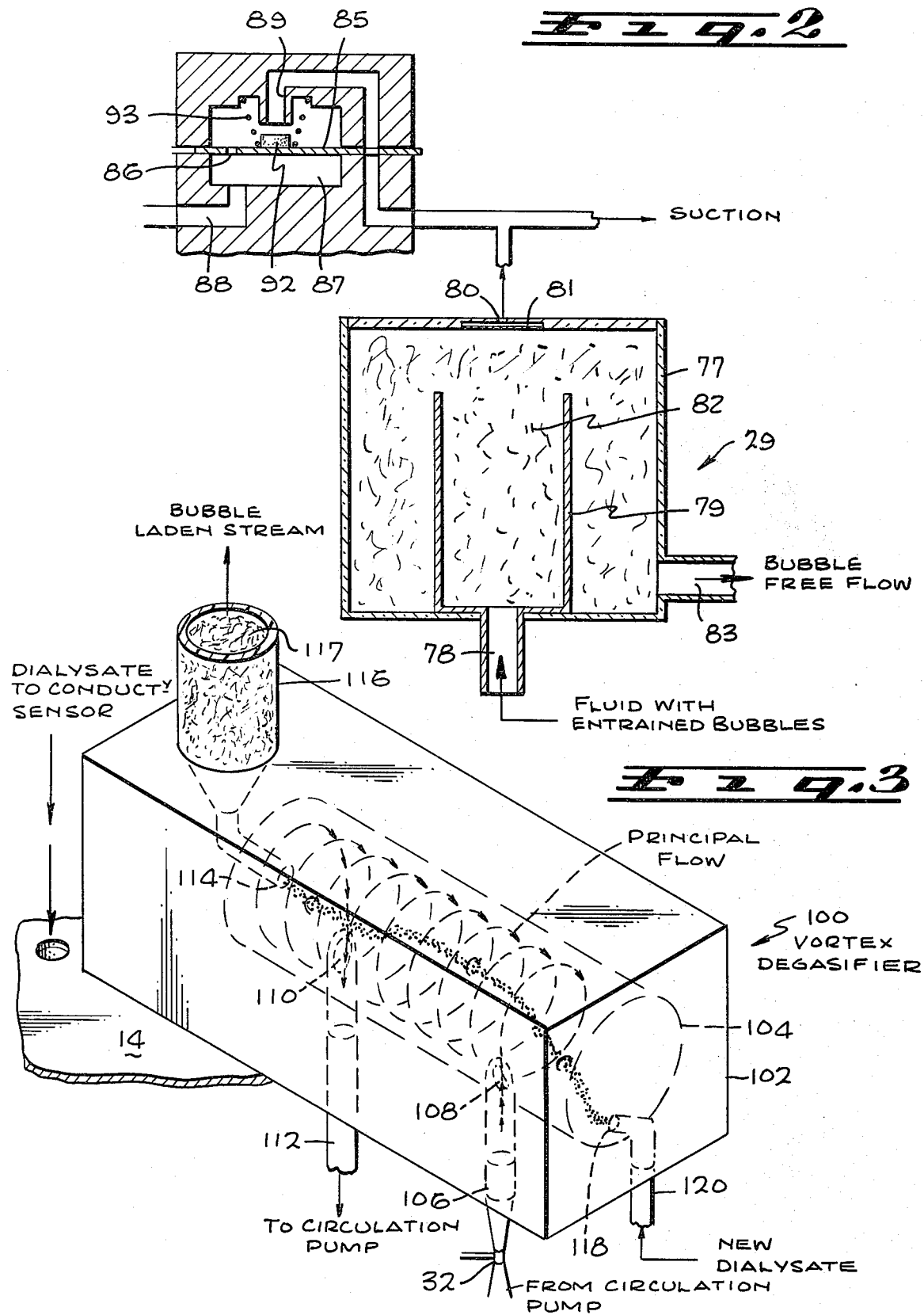

HEMODIALYSIS SYSTEM

BACKGROUND OF THE INVENTION

1. Field of the Invention

This invention relates to the field of hemodialysis, and, in particular, the invention relates to sterilizable dialysis systems using either coil or plate type dialyzers.

2. Description of the Prior Art

Hemodialysis systems are used for blood purification when a patient's kidneys no longer perform adequately or have been surgically removed. In hemodialysis, the patient's blood is circulated on one side of a large surface area membrane having microscopic pores through which waste products from the blood may pass but which are too small to permit passage of essential blood components. Opposite the blood side of the membrane is an isotonic fluid which is circulated to remove the waste products by dialysis. The salt or mineral concentration of the dialysate solution determines the rate and character of absorption of minerals from the blood. A pressure differential across the membrane controls water removal from the blood by reverse osmosis. Numerous critical parameters must be carefully monitored and adjusted to avoid trauma to the patient.

One of those factors is the specific concentration of dialysate solution. If the solution is too weak, excess minerals as well as uremic wastes may be extracted from the blood and the blood cells may be damaged. If the concentration is too strong, the salts may become absorbed by the blood with a resulting toxic effect. However, the cost of the concentrate itself is a significant factor in the total cost of dialysis.

Blood temperature and pressure must also be carefully maintained. Blood temperature maintenance requires precise monitoring of the dialysate temperature inasmuch as the dialysate is in heat exchange relationship to the blood as it passes across the membranes. Pressure is affected by the passage of blood through the dialyzer and depends upon the type of dialyzer and blood pump if used. Water removal from the blood is dependent on the pressure differential across the dialyzer membranes. It is vital that the dialyzer not become clogged, either with air or impurities which would prevent its functioning in transferring uremic wastes to the dialysate solution.

Apparatus which is used in connection with more than one patient requires sterilization. One difficult problem associated with use of medical equipment in the past has been the elimination of microbial organisms such as type B hepatitis. Sterilization in the past has usually been effected by hot water at about 85° C. or by the use of formalin or sodium hypochlorite solution. Neither of these sterilization techniques is sufficiently effective to eliminate type B viral hepatitis. Because of their relatively large size, most dialysis systems are impractical to sterilize by autoclaving techniques.

Two main types of dialyzers are in current use. One is the so-called coil type artificial kidney or dialyzer which consists of a single tubular membrane which has been flattened considerably to provide high and efficient surface area for osmotic transfer between the blood and the dialysate solution. Since the blood must travel a considerable length through the elongated coil dialyzer, a blood pump is required. A substantial flow rate about the outside of the dialyzer kidney provides efficient dialysis. Proportional control of the dialysate has not been employed in this type of system. Typically, a number of the coil-type dialyzers are fed in parallel from a large central mixing station.

Parallel plate dialyzers utilize a multiple membrane stack between the membranes of which blood and dialysate flow in adjacent passageways. Since blood travels a shorter distance across a greater total cross-sectional area than with a coil dialyzer, blood trauma is less likely to occur and the shorter distance often requires less in the way of pumping pressure requirements. However, when a parallel flow dialyzer is used a negative pressure system is required to pull dialysate through the dialyzer. Principally because of such factors, proportional control of dialysate has been employed, but recirculation has not been, in parallel flow systems.

In the past, economic factors have strongly influenced the use of hemodialysis. One high cost factor is the central mixing room used for coil dialysis. The central mixing room typically requires 1000 square feet of hospital space for the mixing of dialysate solution. Two central processors are required for adequate reliability. Should a central processor become contaminated it must be completely shut down for sterilization. Solutions of sodium hypochlorite or formalin are then used to wash the system. Unfortunately, these chemicals also tend to leave residues which have a somewhat toxic effect on the patient. Typically twenty patients will be delivered dialysate solution from the same central mixing room unit. Extensive plumbing is required to transfer the dialysate solution from the central mixing room to the individual rooms of the patients or to the various beds of the ward. Yet each patient still requires an individual canister of dialysate solution.

Central delivery systems are not generally used with parallel flow dialyzers because this type of dialyzer requires an individual suction or proportioning delivery system. In the past, individual proportioning delivery systems have included servo controls to deliver dialysate within predetermined concentration limits. However, continuous uniform levels of concentration are difficult to achieve since the water and concentrate flows are pumped by separate positive flow devices. Though the long term average of the dialysate solution may not change, the short term proportion may change considerably as the pumping action proceeds. Since each of the separate flow devices have 100% control authority over the separate fluids prior to mixing, a failure of either one results in an immediate corresponding error. Since the delivery system is coupled almost directly to the parallel flow dialyzer minor variations during the cycle of the delivery system are seen at the membranes. These variations may be sufficient to alter the blood conditions to such an extent as to throw the patient into shock if not properly monitored.

Thus the coil and parallel dialyzers each have separate special considerations which must be met for their safe utilization. Economics of hospital operations are such that the dialysis systems in use must be transferred at various times to different patients, yet different patients require the use of different types of dialyzers. Thus, numerous problems are still present in providing safe hemodialysis to patients at moderate costs.

SUMMARY OF THE INVENTION

A self-contained blood dialysis unit in accordance with this invention generally comprises a proportioning pump, a canister, and different dialysate flow paths. In one path, the proportioning pump receives an inlet water flow and an inlet saline concentrate flow and feeds dialysate solution to the interior of the canister in specific proportions of concentrate and water, maintained at controlled temperature. In a separate path, means including a recirculation pump deliver dialysate solution from the canister to a dialyzer to maintain a constant and effective flow that is returned to the canister. The canister allows time averaging of variations in concentrate from the proportioning pump, preventing abrupt changes in dialysate concentration and temperature delivered to the dialyzer. A third negative pressure loop is also provided, utilizing a venturi in operative relation to the recirculating pump to create suction that is balanced to the characteristics of a vortex degasifier coupled in the loop. A plate-type dialyzer operated in a proportioning mode may be coupled into this loop. A circulation pump having a positive pressure flow feeds dialysate solution to either a coil dialyzer in the canister or to a plate-type dialyzer in the suction loop at a rate independent of the feed rate of the proportioning pump. This provides a continuous washing of the dialyzer at high dialyzing efficiency. The negative pressure loop pulls dialysate through blood leak, conductivity and temperature monitoring devices, a passive air separator, and also the plate dialyzer when coupled to the unit. The monitoring devices are employed to control dialysate concentration and temperature and in the generation of alarm signals. In the plate-type dialyzer mode, the coil dialyzer is replaced by a vortex degasifier which establishes a different recirculation loop to the circulation pump. Thus, the system may be used with either a coil-type dialyzer or a parallel plate dialyzer and provide all of the functions desirable for each.

To sterilize the system, liquid in the canister is drained, a pressurizing hood is clamped over the canister, and shunts for the dialyzer connections are inserted in each of the flow paths. The heater is vertically arranged such that a limited upward water flow is converted to steam with high efficiency, and the steam is fed throughout the positive and negative pressure flow paths toward a pressure relief valve set at a desired equilibrium pressure. The canister is sterilized on all exposed surfaces, and the circulation pump is also sterilized by redirection of the flow such that steam passes through the pump before entering the canister volume.

Methods of sterilization in accordance with this invention initiate with the heating of water to generate steam that is fed into the conduit system. Steam is flowed through the multi-branch liquid flow path to be sterilized, but the maximum pressure developed within the flow path is controlled while maintaining pressure-temperature equilibrium. This provides a uniform sterilizing temperature throughout the branches of the liquid flow path, which includes both upwardly directed passageways and downwardly directed passageways. The steam rises and passes through the upwardly directed passageways by gravity, but pressure forces out the liquid in the downwardly directed passageways, to assure that the entire flow path is permeated by steam. Liquid retaining regions of the flow path which have interior dialysate contacting surfaces are sterilized by the steps of evacuating liquid from the region under steam pressure less than the equilibrium pressure prior to reaching the sterilization equilibrium temperature. Steam is then passed through to permeate and sterilize the dialysate contacting surfaces of the evacuated retaining region.

Additional aspects of the method for sterilization of the hemodialysis system in accordance with this invention include the passage of steam along a dialyzing flow direction of the positive pressure flow path and the passage of steam in opposition to the dialyzing flow direction in the negative pressure flow path. To achieve sterilization, the interior flow paths are heated to 120° C. and maintained under the pressure of at least 15 psi (1.1 bar). This may become accomplished for the typical system when utilizing a heating element of about 1500 watt by flowing water to the heater at a rate on the order of 50 milliliters per minute to convert approximately one-half of the water flowing therethrough into steam.

BRIEF DESCRIPTION OF THE DRAWINGS

A better understanding of the invention may be had by reference to the following detailed description, taken in connection with the accompanying drawings, in which:

FIG. 1 is a block diagram and schematic view, partly broken away, of a hemodialysis system in accordance with the invention;

FIG. 2 is a more detailed diagrammatic view, partially broken away, of a variable orifice device and an air separator used in the system depicted in FIG. 1; and, FIG. 3 is a perspective view, partially broken away, of a vortex flow degasifier used in place of the coil dialyzer in FIG. 1 when the system is operated with a plate dialyzer.

DETAILED DESCRIPTION

With particular reference to FIG. 1, an example of a hemodialysis unit 10 in accordance with the invention generally comprises a proportioning pump 12 coupled to provide a dialysate solution at a regulated concentration to a canister 14 disposed on the superior surface of the instrument. The proportioning pump 12 may be of any suitable type such as that normally used with parallel plate dialyzers, but an advantageous system is provided by a unit constructed in accordance with a concurrently filed application of Robert L. Anderson entitled "Proportioning Pumping System For Dialysis Machines". The criticality of short term concentration variations is reduced considerably by the use of the canister 14 allowing time averaging in the mixed dialysate path of variations of dialysate provided by the proportioning pump 12. The hemodialysis unit 10 may separately use either a plate or a coil-type dialyzer, both being disposable items, but maintains proportioning in each mode. When a coil dialyzer 16 is used, it is situated within the canister 14 but receives its flow in an independent power loop from a rotating, impeller type, circulation pump 18 driven by a motor 19. The circulation pump 18 removes dialysate from the canister 14 and pumps it under positive pressure so that the dialysate flows across and washes the outer surfaces of the coil dialyzer 16 disposed within the canister 14. Dialysate passing upwardly about the outer dialyzer surfaces spills over into the canister 14 to be recirculated, so that the principal portion of the dialysate is kept in the power loop by a conduit 17 return to the pump 18. The proportioning pump 12 supplies fresh dialysate at a volumetric replenishing rate to the canister 14. Simultaneously, a portion of the continuously replenished dialysate is drained through the upper end of an upright drain pipe 20 in the canister 14, the dialysate in the canister 14 being replenished by the fresh dialysate at the volumetric replenishing rate.

A third, negative pressure, flow loop is independent both of the positive pressure recirculating flow and of the feed flow from the proportioning pump 12 to the canister 14. In this suction loop, dialysate is serially drawn from an orifice in the bottom of the canister 14 through a conductivity cell 21 and temperature monitor 22, an adjustable flow control 24, a negative pressure gauge 26, a plate-type or parallel flow dialyzer 28 (when connected to the unit), an air separator 29, a blood leak detector 30, and a variable orifice 31. Because it is used with minimal blood pressure in the dialyzer, the parallel flow dialyzer 28 requires maintenance of a negative pressure on the solution to prevent accidental passage of potentially toxic dialysate solution into the patient's blood. Negative pressure on the solution also provides a sufficient pressure differential so that adequate water is removed from the blood.

Negative pressure is established at the blood leak detector 30 and the air separator 29 by couplings to a venturi restriction 32 in the conduit between the circulation pump 18 and the canister 14. The one end of the negative pressure loop that is coupled to the outlet in the canister 14 thus receives dialysate, while the other end of the negative pressure loop is coupled to the venturi restriction 32 to draw dialysate through the loop under negative pressure.

In the feed flow path, a water heater 34, comprising an elongated casing 36 of high temperature metal such as Incoloy or stainless steel having an internal resistive heating element is disposed at the inlet end of the positive pressure flow path. The resistive heating element provides an active region for heating water surrounding the casing 36. The water heater 34 is vertically disposed, with a water inlet adjacent its lower end and an outlet adjacent its upper end, both of these being open to a cylindrical region between the casing 36 and an encompassing stainless steel sleeve 38 so that water travels vertically upward through the cylindrical region. This insures that water always surrounds the heated region of the casing 36 (depicted by broken lines) and the unheated end regions to prevent burnout of the internal resistive heating element. In this particular example, the heater generates 1500 watts of power to provide sufficient steam to sterilize the system by techniques in accordance with the invention over a relatively fast period of time (e.g. 20 minutes) while staying within the capacity of conventional household and hospital electrical systems. In response to the temperature level sensed by the temperature monitor 22, temperature servo circuits 37 control the heater 34 so as to maintain the dialysate temperature in a selected range. The water heater 34 thus both supplies steam to the flow path for operation in the sterilization mode, and heats the dialysate to a controlled temperature.

The proportioning pump 12 supplies water to the inlet of the heater 34 at a flow rate proportioned to the concentrate flow rate. A conduit 40 from the heater outlet directs water flow and concentrate received from the proportioning pump 12 through a one-way valve 41 to the canister 14. The proportioning pump 12 is adjustable to give selected water/concentrate ratios, through proportioning servo circuits 39 which generate corrective signals in accordance with the reading of the conductivity cell 21.

A tap water inlet 42 to the hemodialysis unit 10 is coupled by a conduit to a pressure reducer 43, which lowers the pressure to a selected range, such as on the order of 20 psi (1.4 bar). The outlet of the pressure reducer 43 is coupled to a solenoid actuated slide valve 44 having two outlet positions, one for the dialyzing mode and the other for the sterilizing mode. An adjustable flow meter and valve 46 couple the dialyzing mode outlet of the solenoid actuated slide valve 44 to the proportioning pump 12. The flow meter portion provides a visual readout of water flow rate, and flow rate may then be adjusted by a control knob 47 on the flow meter valve 46.

The proportioning pump 12 has a concentrate inlet which is coupled to a concentrate line 48 on the unit 10, and receives water for mixing with a concentrate via the flow meter valve 46. An additional conduit 49 couples the dialyzing mode outlet of the slide valve 44 to a water power inlet to the proportioning pump 12, to provide power for its operation. When the solenoid is actuated to place the slide valve 44 in the sterilization mode, water is directed by a conduit including a flow restriction 45 to the inlet to the heater 34.

The circulation pump 18 comprises a pumping chamber 50 having an inlet coupled to the conduit 17 return from the canister 14, and communicates through the venturi 32 with an outlet fitting 52 (not shown in detail) at the canister 14 for connecting to the coil dialyzer 16. A separate drain conduit 51 is used during sterilization.

The canister 14 is an elongated upright uncovered clear cylindrical container, which may be of polycarbonate "LEXAN" or another suitable transparent material. The upright pipe 20 in the canister 14 is coupled to a drainage outlet 62 via a drain pipe 64 including an upwardly extending portion which receives the upright pipe 20 which is movable between two positions therein. The upright pipe 20 has an aperture 66 adjacent its lower end for draining liquid from the canister 14 when it is moved to an upward position for the sterilization mode. Canister drainage occurs when the aperture 66 is exposed within the canister 14, allowing dialysate to flow through the aperture 66 and down into the drain pipe 64. When the upright pipe 20 is in a downward position, the aperture 66 is closed and excess dialysate is allowed only to overflow into the top of the upright pipe 20 and into the drain pipe 64. In the dialysis mode, the drain line 64 is held open at a shut off valve 65, but this valve 65 is closed for the sterilization mode.

When sterilizing also, a hood 68 is mounted over the canister 14 after it is drained. The hood 68 is of sterilizable material such as stainless steel, preferably cylindrical in shape and has an outer circular lip to engage a conforming surface (not shown in detail) on the upper portion of the unit 10. Holding means 70, shown symbolically as screws but preferably comprising wedging clamps that may be engaged with a partial turn, are disposed on the sides of the hood 68 for locking the hood 68 into position over the canister 14 to pressure seal the system during the sterilization mode. The hood 68 has a height somewhat greater than that of the canister 14 to prevent canister interference and to allow steam to contact both the interior and exterior exposed surfaces of the canister 14 during the sterilization mode. The hood 68 also includes a safety valve 71 to allow for the release of steam at a design pressure of for example 25 psi which is in excess of the equilibrium pressure used during sterilization.

A steam pressure activated relief valve 72 having a release pressure on the order of 15 psi at sea level is coupled to the drainage outlet 62 in shunt with the shut off valve 65. Normally the relief valve 72 is bypassed by the open shut off valve 65 in the dialysis mode. However when sterilizing, the shut off valve is closed and relief valve 72 allows pressure to develop to 15 psi. The steam being under pressure causes the temperature to rise to a sterilization temperature of about 120°, at which sterilization equilibrium is achieved throughout the entire system.

A 10 psi drain relief valve 74 couples the drain conduit 51 to the lower end of the pumping chamber 50 with the drain pipe 64 for drainage of any liquid dialysate solution remaining therein prior to achieving pressure-temperature equilibrium in the sterilization mode. The relief valve 74 has a design pressure lower than that of the pressure relief valve 72, such that as pressure is developed the valve 74 opens at 10 psi and the steam pressure forces liquid remaining in the lower portion of the pumping chamber 50 and through the drain outlet 64. Relief valves of the same or similar pressure may also be utilized at other branches in the system to eliminate liquid from lower liquid retaining regions of the system, where steam would otherwise not penetrate.

The conductivity cell 21 and temperature monitor 22 provide indications of the salinity or concentration and the current temperature respectively of the dialysate solution. Conventional devices and circuits may be used in each. For example, a thermistor (not shown) in the flow path may be coupled to an ordinary bridge circuit including a meter for monitoring temperature. In the temperature servo circuits 37 the bridge may be coupled to a zero crossing detector which controls a relay for turning the heater 34 on and off to maintain temperature control. High and low temperature conditions in the dialysate solution affect the rate of transfer of uremic waste. In addition, temperature also affects the blood condition so that inappropriate temperatures can induce blood trauma. The use of a canister further permits the employment of a switching approach because temperature changes are time averaged in the canister 14 bath.

Similarly, the concentration of the dialysate must be carefully controlled to maintain isotonicity assuring one way osmotic transfer across the membranes. The conductivity cell 21 may be of any suitable type currently in use in hemodialysis systems, but preferably is of the type described in co-pending application Ser. No. 599,691, filed July 28, 1975, entitled "Conductivity Cell", Robert L. Anderson, and assigned to the inventor herein. Whatever type of conductivity cell is employed, the signal derived is used in the proportioning servo circuits 39 to generate an appropriate corrective signal so as to tend to maintain the concentration at a reference level selectable at the operator's option. Conventional controls and panel indicators for the temperature and concentration functions have not been shown for simplicity.

The adjustable flow control 24 includes a threaded adjustment knob coupled to an adjustable shaft 73 having a tapered tip. A flow path normally established between the inlet and the outlet of a flow chamber 76 in the negative pressure control device is selectively restricted by the end of the shaft in the flow path. In addition, a bypass restriction 75 shunting the inlet and outlet of the flow control 24 establishes a lower limit on the minimum pressure available so that a certain minimum flow is always maintained. The flow path from the negative pressure control 24 is connected to the negative pressure sensor and gauge 26. This provides a visual indication of the pressure passing through the negative pressure loop so that the flow control may be manually adjusted. The sensor and gauge 26 may include a diaphragm separated from the indicator mechanism so that dialysate contacting surfaces of the negative pressure gauge 26 may be fully sterilized in isolation from the indicator mechanism. Although the maximum suction available is dependent upon the recirculation flow of the circulation pump 18, the suction pressure is independently adjustable by means of the flow control 24.

The air separator 29, referring now to FIG. 2, comprises a cylindrical housing 77 having a bottom central inlet 78 for receiving dialysate having entrained bubbles. Concentric with the housing 77, but to a lesser height, the inlet 78 is encompassed by an internal tubular flow guide 79. A small suction outlet 80 in the top wall of the housing 77 opposite from the inlet 78 is coupled to the suction line to remove dialysate solution rich in dissolved gases in the form of large bubbles. A protective screen 81 is disposed across the suction outlet 80 to provide isolation from steel wool 82 filling the chamber interior. The internal tubular flow guide 79 is typically stainless steel and first carries the dialysate up, before it flows down outside the flow guide 79 to an outlet aperture 83 adjacent the housing 77 bottom. The stainless steel wool 82 between the flow guide 79 and the lower outlet 83 traps bubbles traveling through its volume. As the dialysate flows upwardly in the center region some bubbles rise to the suction outlet 80, particularly the larger bubbles having adequate buoyancy. The downward flow of dialysate outside the flow guide 79 occurs within a larger volume which slows down the flow velocity so that it is less than the terminal upward velocity, due to buoyancy, of a substantial proportion of the bubbles. Moreover, under these conditions the more minute bubbles tend to be captured on the steel wool 82, coalescing as more bubbles are captured, and ultimately acquiring sufficient buoyancy to escape. The size of the suction hole 80 is chosen such that air plus about 10% of the total flow follows this path. Adjustable orifice sizes may be utilized if desired. The dialysate solution containing large bubbles is passed by the conduit system back into the negative pressure flow path through the venturi restriction 32 and back into the canister 14, in which the large bubbles rise to the surface and are released to atmosphere.

The air separator 29 is a passive device which functions adequately by itself for the coil dialyzer mode, and variations in system design and operating conditions can be accommodated by varying the relative diameters of the internal flow guide 79 and the external flow guide defined by the housing 77. For higher dialysate flow rates in the suction loop, such as are used when a plate-type dialyzer is employed, more energetic air separation must be achieved, and this is described below in conjunction with FIG. 3.

It should be noted that the suction loop comprises an important part of the system but utilizes only negative pressure from the venturi for flow maintenance. Because of the number of elements in this loop, varying operating conditions can tend to introduce changes in suction, which in most systems is troublesome because flow falls off at higher suction. In the present system, however, suction flow is automatically regulated, for a given setting, by a variable orifice device 31, also shown in FIG. 2. The variable orifice 31 comprises a thin flexible diaphragm 85 having a flow aperture 86 of fixed size, and mounted to span a flow chamber 87 having an inlet orifice 88 on one side and a central outlet orifice 89 on the other. The outlet orifice 89 is in the form of a boss facing an opposed seal 92 mounted on the diaphragm 85, with the diaphragm 85 being biased against closure by an encompassing spring 93.

When suction is drawn on the outlet orifice 89, a small differential pressure exists across the diaphragm 85 because of the flow restriction introduced by the fixed orifice 86. The pressure difference tends to close the variable orifice defined by the end surface of the outlet orifice 89 and the facing seal 92. The greater the suction, the greater the deflection of the diaphragm 85, and the smaller the size of the variable orifice. Thus because the variable orifice is inversely related to the suction level, the flow rate is automatically compensated. At high suction the orifice is small and the flow rate which would tend to be high is reduced to a selected nominal level; in contrast if suction goes low the variable orifice opens to permit more ready flow and equalize at the nominal level.

The blood leak detector 30 is coupled to the parallel flow kidney to detect any leakage of blood through the membranes of the parallel flow kidney, and activates conventional alarms (not shown). The blood leak detector may be of any suitable type or the type described in a co-pending application of the invention herein, entitled "Blood Leak Detector", filed July 18, 1975, Ser. No. 597,243. For safety purposes, it is also conventional to use a concentrate monitor 95 at the concentrate line 48 to insure that the concentrate supply is present during operation.

The presence of a substantial proportion of minute bubbles in the dialysate during operation with a plate-type dialyzer is detrimental to system operation in a number of respects. Foremost of these is the inaccuracy which results in the readings of the conductivity sensor, arising from collection of bubbles on the inner walls of the device. The passive air separation device described in conjunction with FIG. 2 is not effective for purposes of elimination of the minute bubbles under high flow rate conditions, when the presence of minute bubbles is visibly evidenced as an increased opacity or cloudiness of the solution. Larger bubbles which can readily be perceived by the unaided eye are not the problem, because these have sufficient buoyancy to rise to the top of the dialysate bath. However, the minute bubbles do not have sufficient volume and therefore buoyancy to overcome the fluid viscosity, particularly in the presence of currents. Thus the minute bubbles move through the system, including the air separation device, and gradually accumulate on the inner surfaces of the conductivity sensor, there being insufficient fluid velocity to keep these surfaces wiped clean.

In accordance with the invention, the recirculation loop for the dialysate bath is employed for degasification during usage of a plate-type dialyzer, by simply replacing the coil-type dialyzer of FIG. 1 with a vortex flow degasifier 100, as seen in FIG. 3. The vortex unit comprises a housing 102 which may advantageously be of a transparent material to view the degasification process, and which may be sectioned (not shown) for easy fabrication. Within the housing a central chamber 104 of circular cross section is disposed about a central axis that is substantially parallel to the plane of the base of the canister 14 in this example. The circular cross section need not be uniform, although a cylindrical chamber is shown in FIG. 3, and in fact conical chambers may be employed as described hereafter. The vortex degasifier includes conduit couplings to several of the apertures in the canister 14, and for ready insertion and removal may be mounted with O-ring fittings (not shown), as may be the coil dialyzers that are attached. One coupling 106 is made to the conduit from the venturi 32 and circulation pump (not shown), and terminates in a dialysate injection port 108. The injection port 108 is directed approximately tangential to the peripheral margin of the chamber 104, and approximately normal to the central axis. Thus dialysate is injected into the chamber 104 with a circular motion about the central axis.

Adjacent the opposite end of the chamber 104, an outlet port 110 is disposed tangential to the peripheral margin of the chamber 104, but positioned so as to receive the circular flow axially. The outlet flow is passed through a coupling 112 into the system conduit that returns to the circulation pump. In a central region of the end surface of the chamber 104 that is closest the outlet port 110 is disposed a gas port 114 facing the direction of the central axis. The gas port 114 leads to an enlarged ejection conduit 116 containing stainless steel wool 117 through which bubble laden dialysate comprising a small part (of the order of 10%) of the dialysate is delivered from the vortex flow degasifier. Additionally a small inlet port 118 angled to be tangential to the inner circular flow is disposed adjacent the same end as the injection port 108 and is in communication with a coupling 120 to the heater and proportioning pump (not shown), whereby fresh dialysate is fed into the system.

In operating in the plate dialyzer mode, therefore, the vortex flow degasifier 100 is used as a direct replacement for the coil dialyzer of FIG. 1 (and a plate dialyzer is attached at its appropriate connections). As operation begins, fresh dialysate enters the degasifier 100 through the inlet port 118 and carries with it substantial amounts of dissolved gas, essentially air. The chamber 104 fills quickly, and as it does some of the dialysate is extracted from the outlet port 110 and returned to the circulation pump, from which it passes through the venturi 32 into the injection port 108, and thus back into the chamber 104 at high velocity. Recirculation then takes place continuously. The injected flow quickly establishes a vortex flow approximately about the central axis of the chamber 104, with the dialysate following an at least approximately helical path as shown, and establishing a high angular velocity at the periphery. Immediately about the central axis, however, the angular velocity is even greater. Two effects act to bring the bubbles toward the center of the chamber. Centrifugal separation forces the heavier constituents (i.e. dialysate) outwardly relative to the lighter constituents (i.e. gas), and a narrow rotating bubble stream is defined from approximately the inlet port 118 to the gas port 114. The bubble stream, as shown in FIG. 3, tends to overshoot the central axis before becoming aligned approximately with the central axis just before the gas outlet port 114, and moves quite rapidly from one end of the chamber 104 to the other. The visible and spinning bubble flow represents the accumulation of small bubbles at the center region into large bubbles which readily float up through the dialysate. The turbulence of the flow, and within the bath, and the content of minute bubbles, are reduced substantially by the inclusion of stainless steel wool 117 in the enlarged outlet conduit. Large bubbles pass freely through the conduit 116 while small bubbles coalesce into larger ones and then float to the surface.

The additional effect to be observed is that the bubble stream is stabilized despite the turbulent flow, because shear forces created by the different angular velocities at different radii limit the ability of bubbles to escape outwardly. After the vortex flow degasifier 100 has been in operation for a short time this degassing recirculation flow perceptibly clarifies an opaque dialysate, and continues the clarification with constant diminution of the gas level. The dialysate, viewed through a clear canister under strong illumination, is in the steady state seen to have a minimal amount of contained gases present, even as minute bubbles. Experimental measurements have also been taken to the accuracy of the conductivity sensor, and these measurements confirm reduction of contained gases to a level at which there exists no discernible drift or other effect on conductivity readings.

Thus the system is arranged such that the suction loop fulfills unique and different functions when operated with a parallel or plate-type dialyzer in contrast to a coil-type unit. In the coil mode, the suction loop needs only relatively low flow rates sufficient for the various sensing functions to be performed. Consequently the air separator 29 can function as a passive device having sufficient capability for removing bubbles from the dialysate. With a plate-type dialyzer connected and the coil unit removed, however, the flow rate in the suction loop is adjusted to be high enough to permit adequate interchange at the membrane surfaces. Consequently, passive air separation does not make available sufficient separation energy to eliminate the deleterious minute bubbles (except if the passive device is made unacceptably large). However, at the higher flow rates the vortex degasifier 100 uses the dynamic flow itself to achieve an adequate level of degasification.

Note that although the vortex degasifier is interchangeable with the coil unit, a substantially different flow path is established in the plate dialyzer mode. Instead of directing dialysate into the canister 14 bath through the coil unit, and then withdrawing dialysate back into the pump from a different point in the bath, the major dialysate flow is directly returned to the pump. Only a small proportion is transferred into the bath, but because the gas concentration has been formed into large bubbles, these float immediately to the top of the bath and are vented.

Further in accordance with the invention, certain interrelationships should advantageously be observed in the vortex degasifier configuration. In order to achieve adequate separation, the angular velocity of the dialyzer should be of the order of 1000 radians/sec, and in general between 500 and 1500 radians/sec. While the capacity of the pump and the size of the venturi establish the flow rate, the flow impedances in the system must not react upon the venturi. For example, some coil dialyzers have small entry orifices which would create back pressure on a venturi of comparable size, reducing the effectiveness of the venturi action. In addition, two primary considerations should be observed to maintain a proper degasification action. For the desired concentric flow pattern, the diameter of the circular chamber should be from approximately 3 to 5 times the diameter of the injection orifice. In the practical example shown the ratio was slightly greater than 3. Also, to control the entrained bubble stream to the exit, the length of the chamber, between injection and outlet port centers, should be from 3 to 5 times the injection port diameter. A value of 5 was employed in the example shown.

There are, however, other variables which can be employed to enhance or stabilize the degasification function. The circular chamber may expand outwardly in diameter in the direction toward the exit end; alternatively or concurrently the outlet port may be shifted in position so that it is not directly in line to receive the revolving liquid (i.e. it may be moved to the same side, relative to the central axis, as the injection port). Each of these expedients has the effect of slowing down the outer liquid flow near the exit end while not appreciably affecting the angular velocity directly adjacent the bubble stream, because the former increases the cross-sectional flow area and the latter acts as a brake on flow at the outer periphery. Each expedient therefore contributes to establishment of a shear barrier arising from the differential angular velocities in the region approaching the exit end, and this shear barrier aids in confinement of the axial bubble stream.

The significance of the establishment of a recirculating flow path for a plate-type dialyzer should also be appreciated. In prior art systems without recirculation a constant flow of fresh dialysate is employed (typically about 300–500 ml/minute). In the present system, in contrast, a substantially higher flow rate of dialysate can be employed at the membrane. The recirculating suction loop feed rate which passes through the dialyzer is independent of the fresh feed flow rate, and is typically held in the range of 800 ml to 1 liter/minute. A high flow rate at the membrane reduces surface layer boundary effects and markedly improves osmotic transfer at the membrane. The resultant improvement in dialysis efficiency more than overcomes loss factors arising from the fact that there is a partially spent constituent in the dialysate. It must be recognized, however, that there are differences between the clearance of large molecules and small molecules, and that improvements in the transport efficiency involve complex relationships. Substances of relatively lower molecular weight, such as urea and creatinine, are transferred with relatively high efficiency, so that these quickly appear in the recirculating solution and efficiency decreases somewhat as to these constituents. Larger molecules, and particularly constituents such as vitamin $B_{12}$ and inulin (which have molecular weights of approximately 1,000 and 5,000 respectively) are cleared with a higher efficiency rate than with existing systems. Clinical testing has shown, for example, a decrease in clearance efficiency of approximately 25% for urea and creatinine, in contrast to an increase of approximately 12% for vitamin $B_{12}$ and 15% for inulin. While the susceptability of patients to different toxic wastes may vary, the constituents of smaller molecular wastes are generally less troublesome and investigations seeking an enhanced ability to clear constituents of higher molecular weight have been undertaken independently. In any event, the option of being able to utilize a substantially higher permeation rate enables the urologist to take advantage of machine characteristics for specific patients in accordance with their individual requirements.

The structure in accordance with the invention can, moreover, be utilized without substantial modification in a non-recirculating mode. For this purpose, dialysate would be degasified using a pumping degasifier of the type disclosed in a pending patent application entitled "Liquid Degasifier System And Method", Ser. No. 653,229, filed Jan. 29, 1976, Robert L. Anderson, and the flow would then be directed from the heater 34 to the conductivity cell 21 and the outlet from the suction device such as a venturi would be sent directly to the drain. If a venturi is used, some proportion of the flow is typically employed to establish the venturi effect, but other types of suction devices might alternatively be used. It is evident, however, that only a few connections are required to operate in a non-recirculating mode, and that the system may be internally sterilized as described hereinafter.

The provision of a proportional type of coil dialyzer also affords unique advantages in comparison to previously known systems. Conditions of system operation may be varied so as to conform to the needs of an individual patient, unlike conventional central delivery systems. If a substantial number of patients are to be placed on coil dialyzers, adequate reliability is assured merely by having one or two extra machines. The cost of each is comparable to the individual coil dialyzer stations and at a small fraction of the cost of a single central delivery system, without regard to the redundant central system which must be kept on hand for safety purposes.

When the system is operated in a sterilizing mode referring again to FIG. 1, a steam shunt 124 is coupled across fittings (not shown in detail) at the inside of the canister 14 to direct steam flow from the heater 34 directly to the circulation pump 18. A separate steam shunt 126 is applied across the plate dialyzer fitting (or across the ends of connector tubes, if used, to insure their sterilization), and the outlet fitting 52 coupling the circulation pump 18 to the canister 14 is blocked by a seal 128 so that steam is forced through the circulation pump 18 rather than back into the canister 14. The shunts 124, 126, and the blocking seal 128 are used to force the steam through a uniquely defined flow path since steam, being lighter than air travels upward but will not travel downward as certain of the flow paths are positioned, unless forced to do so. In FIG. 1, it will be noted that an arrow with an "S" indicates the direction of flow in the sterilization mode, to distinguish from the dialysis mode, designated by an arrow with a "D".

To initiate sterilization, the circulation pump 18 is turned off. The upright pipe 20 is raised to allow drainage of dialysate from the canister 14. The manually operated shut off valve 65 is held open to allow flow of solution to the drain. Then the steam shunt 124, the plate dialyzer shunt 126 and the blocking seal 128 for the coil kidney fitting are secured. The circulation pump 18 is then turned on. In order for water to bypass the proportioning pump 12, the solenoid valve 44 is activated to the "sterilize" position. Tap water flows through the valve 44 and through both the positive pressure and negative pressure flow paths. This pre-rinses and flushes the system with water.

The hood 68 is placed on the unit 10 and clamped in place and the safety valve 71 is positioned on the hood 68. The heater 34 is turned on and the recirculation pump 18 is turned off. The shut off valve 65 is then closed so that escaping fluid, whether steam or dialysate, must pass through the 15 psi relief valve.

Tap water continues to be passed through the pressure reducer 43, reducing the pressure to 20 psi, and then the solenoid actuated slide valve 44 directs water flow through the conduit restriction 45 and then to the water heater 34. Water flows through the heater 34, and approximately 50% of the water is converted into steam, which is entrained with the water entering the flow path.

The system is designed to convert to steam only a portion of the water entering the heater, to provide sufficient latitude both to maintain pressure-temperature equilibrium, requiring the presence of both steam and vapor phases in the system and also to avoid the possibility of overheating the heater casing 36.

Water completely surrounds the heater casing 36 and travels vertically upward. The heater 34 is upright to prevent formation of stagnant gas pockets which would burn out the heater. The steam bubbles enclosed by water travels through the flow path and upward to the canister 14. Upon reaching the canister 14 it is immediately shunted by the steam shunt 124 to the circulation pump pumping chamber 50. As pressure is built up within the pumping chamber 50, liquid that is physically above the entry level of steam is sputtered through the negative flow path. Liquid beneath the level of the entry to the pumping chamber 50 is forced downward through the pressure responsive drain valve 74 after its design pressure is exceeded, and out through the drain 62. Since the venturi restriction 32 opening to the canister 14 is blocked by the seal 128, the steam is forced to travel through the negative pressure flow path in the opposite direction of dialysate solution flow. As shown by the flow arrows, the steam generally travels in the same direction as the dialysate solution in the positive pressure flow path. Dialysate solution traveling downward through the negative pressure flow path travels first through the variable orifice 31 and the blood leak detector 30. The shunt 126 applied across the parallel flow dialyzer fitting directs steam through the principal flow path of the air separator 29, thence through the dialysate contacting surfaces including the diaphragm of the negative pressure gauge 26 and through the negative pressure control 24. The steam then flows through the temperature monitor 22 and conductivity cell 21 and is directed upward into the canister 14. Since the hood 68 is latched in place, the entire inside and outside exposed dialysate contacting surfaces of the canister 14 are permeated with steam. Should excess pressure be present within the canister 14, the safety release valve 71 opens allowing steam to escape.

As steam is generated in the multi-branch flow path, pressure begins to build. As the pressure reaches 15 psi, the relief valve 72 adjacent the drain opens, and conversely when pressure drops below 15 psi the pressure relief valve 72 closes. The opening and closing of the valve 72 at this pressure maintains the temperature within the entire flow path at approximately 120° C., although it should be borne in mind that pressure/temperature conditions are affected by the altitude in which the hemodialysis unit is used. A pressure/temperature equilibrium is assured by converting only a part (here about 50%) of the water passing through the heater into steam while the rest of the water remains liquid.

Sterilization is a simple procedure which may be performed by a medical technician. A temperature of 120° C., maintained at equilibrium for about 20 minutes, has been found sufficient to destroy all known forms of microbial organisms thereby allowing the transfer of the hemodialysis unit from patient to patient. Since the unit is relatively compact, expensive hospital space may be saved with resultant cost savings. The hemodialysis unit is versatile in that it allows use with either a coil-type dialyzer or a plate dialyzer.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A compact hemodialysis system including a dialyzer comprising:

canister means having an interior chamber for receiving a dialysate solution and means for draining solution in excess of a selected amount;

a proportioning pump responsive to control signals for feeding dialysate solution to the interior chamber of the canister means, the proportioning pump receiving an inlet water flow and an inlet saline concentrate flow and providing outlet water and concentrate flows in specific proportions comprising a feed rate flow of dialysate solution;

circulation pump means including conduit means coupled to the canister means for delivering dialysate solution to the dialyzer at a rate which may be independent of the feed rate flow;

means for returning the solution through the dialyzer to the canister means, the canister means time averaging variations in concentrate from the proportioning pump to prevent abrupt changes in dialysate properties delivered to the dialyzer and draining off excess from the canister means;

means including conduit means coupled to the circulation pump means and to said canister means for defining a suction loop, the suction loop including negative pressure means for circulating the dialysate solution from the canister means in the suction loop independent of the feed flow from the proportioning pump to the canister means, and wherein the suction loop in addition include means responsive to the dialysate for providing control signals for control of the proportioning pump;

means internal to the hemodialysis system for passing steam throughout the conduit means and the canister means to sterilize the system so that the unit may be used thereafter with different patients without danger of contamination, said means internal to the hemodialysis system comprising a resistive heating element having an exterior casing in the feed flow path, and a cylindrical sleeve about and larger than the casing and means for admitting water at a lower end of the heater between the sleeve and casing and for allowing the escape of saturated steam at the upper end of the heater, the heater being disposed in an upright position so that forced vertical convection drives steam upwardly preventing steam collection and overheating adjacent the heated core surface;

means for shunting exterior couplings of the conduit means to provide a confined pressurizable multipath volume having a drain outlet, a liquid retaining lower cavity along the flow path and a conduit coupled to the drain outlet from the lower end of the cavity, and pressure release means coupled to the drain oulet for regulating the maximum pressure available in the system to develop a pressure-temperature equilibrium upon generation of adequate steam in the presence of liquid water to sterilize the dialysis system by steam at temperatures substantially in excess of the atmospheric boiling point of water to adequately destroy bacterial and viral germs;

means for enclosing the canister means to enable steam to contact all exposed surfaces of the canister means, said means for enclosing including safety valve means operable at a higher pressure than said means for maintaining pressure;

and drain valve means in the conduit having a lower operating pressure than the means for maintaining steam at pressure, so that liquid is driven out of the lower cavity through the drain valve means prior to the flow path reaching equilibrium temperature, and thereby allowing complete flow path surface steam penetration.

2. A blood dialysis system for receiving a dialyzer comprising:

canister means including an upwardly open volume for receiving a dialysate;

feed flow means for delivering dialysate to the canister means at a regulated concentration and at feed flow rate;

circulating flow means comprising a positive pressure flow loop and a negative pressure loop for removing dialysate from the canister means at a rate independent of the feed flow rate to supply dialysate to the dialyzer and returning dialysate to the canister means;

means including a plurality of dialysate monitoring devices in the negative pressure loop to aid in maintaining control over dialysate passing through the dialyzer coupled to the circulating flow means;

a circulation pump in the feed flow means;

venturi means coupling the circulation pump to the canister means, and coupled to the negative pressure loop whereby dialysate pumped by the circulation pump to the canister means provides negative pressure at the venturi means for the negative pressure loop;

negative pressure control means coupled in the negative pressure loop, the negative pressure control means including a limiting restriction and means for adjustably bypassing the limiting restriction, the limiting restriction providing a minimum negative pressure available within the negative pressure loop and the adjustable bypass means allowing increased negative pressure within the loop;

air separator means in the negative pressure loop including an inlet and a spaced apart outlet at lower regions thereof;

an internal upstanding flow guide about the inlet and an outer tubular flow guide of greater volume than the internal flow guide to define a downward flow path with dialysate velocity lower than the upward velocity of a substantial proportion of bubbles entrained in the dialysate;

a suction outlet opening in the upper region of the air separator means spaced apart from the inlet for withdrawing a fraction of the dialysate rich in bubbles; and mesh disposed within the air separator means for collecting and coalescing small bubbles traveling with the dialysate.

3. A self-contained sterilizable hemodialysis system comprising:

canister means for holding a supply of dialysate;

proportioning means coupled to supply dialysate in a feed flow path at a regulated concentration and feed rate to the canister means;

an upright elongated water heater in the feed flow path;

circulation pump means for removing dialysate solution from the canister means at a rate independent of the feed rate in a positive pressure circulation path;

a negative pressure flow path including flow control means coupled to the circulation pump means and the canister means, in which flow path dialysate is drawn through at a controllable rate;

means coupled along the negative pressure flow path for monitoring the concentration of dialysate solution including means providing a signal in response thereto;

means coupled to the proportioning means for adjusting the concentration of dialysate in response to the dialysate monitoring signal;

the system including means for forcing steam generated by the heater through portions of the feed flow path exposed to contamination, the positive pressure circulation path and the negative pressure flow path;

means for receiving either (1) a coil dialyzer in the canister means and in the positive pressure circulation path or (2) a parallel flow dialyzer in the negative pressure flow path;

and degasifier means adapted to couple into the positive pressure circulation path within the canister means when the system is operated with a parallel flow dialyzer.

4. The invention as set forth in claim 3 above, wherein the degasifier comprises a vortex degasifier arranged to create an angular velocity of from 500 to 1500 radians per minute of the dialysate about a central axis, and including means for withdrawing a minor proportion of dialysate containing a substantial proportion of entrained gases at the central axis.

5. A method for sterilizing hemodialysis apparatus having an interconnecting multibranch liquid flow path including upwardly and downwardly directed passageways containing liquid comprising the steps of:

heating water to generate sufficient steam to pressurize the multibranch liquid flow path;

flowing steam generated by the heating step through the multibranch liquid flow path to be sterilized;

limiting the maximum steam pressure developed therein to establish a pressure-temperature equilibrium to supply steam at the same sterilizing temperature throughout the multibranch liquid flow path; and bubbling steam through the upwardly directed passageways using the gravitational buoyancy of the bubbles, while forcing steam under pressure through the downwardly directed passageways.

6. The method as set forth in claim 5 above, in which the interconnecting multi-branch flow paths include liquid retaining regions having interior dialysate contacting surfaces, comprising the additional steps of:

evacuating liquid from the liquid retaining regions under pressure less than the equilibrium pressure prior to attaining sterilizing equilibrium temperature; and thereafter passing steam through the liquid retaining region to permeate and sterilize the dialysate contacting surfaces of the evacuated liquid retaining region.

7. The method as set forth in claim 6 above, wherein thre multi-branch flow paths include a positive pressure liquid flow path and a negative pressure liquid flow path, each of the positive and negative pressure flow paths having a predetermined liquid flow direction during dialysis wherein the step of flowing steam through the multibranch liquid flow path comprises:

passing steam along the liquid flow direction in the positive pressure liquid flow path; and passing steam in opposition to the liquid flow direction in the negative pressure liquid flow path.

8. The method as set forth in claim 7 above, wherein the maximum steam pressure is maintained such that temperature equilibrium is achieved at approximately 120° C., and wherein approximately 50% of the water in the pressurized system is converted to steam.

9. The method as set forth in claim 8 above, wherein the steam pressure is maintained at approximately 15 psi and the water flow rate is approximately 50 ml per minute.

10. A proportioning hemodialysis system for operation with either a coil dialyzer or a parallel flow dialyzer and comprising:

means including controllable proportioning pump means for providing a feed flow;

canister means for maintaining a dialysate bath, coupled to receive the feed flow;

dialysate circulating means coupled to said canister means for maintaining a circulating flow of dialysate, said circulating means including venturi means;

suction loop means coupled to said canister means and said venturi means for maintaining a separate negative pressure flow, said suction loop means including means responsive to dialysate properties for providing a signal to control said proportioning pump means;

controllable heater means coupled in the feed flow;

temperature sensor means coupled in the suction loop means and coupled to control the heater means to regulate dialysate temperature;

whereby (1) a coil dialyzer may be coupled into the circulating flow at said canister means or (2) a parallel flow dialyzer may be coupled into the negative pressure flow; and a vortex degasifier coupled in the circulation flow when the system incorporates a parallel flow dialyzer, the vortex degasifier including a chamber of circular cross-section about a central axis and having inlet and outlet orifices tangentially disposed relative to the interior periphery of the chamber and spaced apart along the length of the chamber and a gas outlet port disposed adjacent and in facing relation to the central axis of the chamber, and further including means establishing an angular velocity of 500–1500 radians per minute in the dialysate therein.

11. The invention as set forth in claim 10 above, wherein the inlet orifice has a diameter D, wherein the length L of the chamber is between 3 D and 5 D, and including in addition conduit means coupled to the gas outlet port and having an enlarged cross-sectional area, and filamentary dialysate permeable means disposed within said conduit means.

* * * * *